United States Patent
Puerta et al.

(10) Patent No.: US 8,362,175 B2
(45) Date of Patent: Jan. 29, 2013

(54) BETA-AMINO ESTER COMPOUNDS AND USES THEREOF

(75) Inventors: David Thomas Puerta, Melrose, MA (US); Susan Alice Williams, Natlick, MA (US); Ronald P. McLaughlin, Reading, MA (US); Daniel Griffith Anderson, Sudbury, MA (US)

(73) Assignee: Living Proof, Inc., Cambridge, MA (US)

( * ) Notice: Subject to any disclaimer, the term of this patent is extended or adjusted under 35 U.S.C. 154(b) by 0 days.

(21) Appl. No.: 13/414,407

(22) Filed: Mar. 7, 2012

(65) Prior Publication Data

US 2012/0164095 A1    Jun. 28, 2012

Related U.S. Application Data

(62) Division of application No. 12/354,697, filed on Jan. 15, 2009, now Pat. No. 8,163,861.

(51) Int. Cl.
*C08F 18/00* (2006.01)
*A61K 8/72* (2006.01)

(52) U.S. Cl. ...................... 526/319; 424/70.1

(58) Field of Classification Search ................. 526/319; 424/70.1
See application file for complete search history.

(56) References Cited

U.S. PATENT DOCUMENTS

| | | | |
|---|---|---|---|
| 5,180,424 A | 1/1993 | Hutter | |
| 5,696,070 A | 12/1997 | Tachizawa et al. | |
| 5,859,268 A | 1/1999 | Angelici et al. | |
| 5,922,909 A | 7/1999 | Joffre | |
| 6,222,062 B1 | 4/2001 | Anderson et al. | |
| 6,348,618 B1 | 2/2002 | Anderson et al. | |
| 6,673,756 B2 | 1/2004 | Sonnenberg et al. | |
| 6,998,115 B2 * | 2/2006 | Langer et al. | 424/78.37 |
| 7,101,538 B1 | 9/2006 | Tang | |
| 7,307,061 B2 | 12/2007 | Shuey et al. | |
| 7,427,394 B2 * | 9/2008 | Anderson et al. | 424/78.37 |
| 2003/0124368 A1 | 7/2003 | Lynn et al. | |
| 2004/0071654 A1 * | 4/2004 | Anderson et al. | 424/78.37 |
| 2005/0265961 A1 * | 12/2005 | Langer et al. | 424/78.36 |
| 2007/0218120 A1 | 9/2007 | Lee et al. | |
| 2008/0267903 A1 | 10/2008 | Uchegbu et al. | |
| 2008/0293827 A1 | 11/2008 | Lee et al. | |

FOREIGN PATENT DOCUMENTS

| | | |
|---|---|---|
| EP | 0310299 A1 | 4/1989 |
| EP | 0728737 A1 | 8/1996 |
| EP | 1837353 A1 | 9/2007 |
| JP | 52045327 A | 4/1977 |
| WO | 9716407 A1 | 5/1997 |
| WO | 9951221 A1 | 10/1999 |
| WO | 2006040579 A1 | 4/2006 |
| WO | 2006109945 A1 | 10/2006 |
| WO | 2007082304 A2 | 7/2007 |
| WO | 2007082305 A2 | 7/2007 |
| WO | 2007127065 A2 | 11/2007 |
| WO | 2008070368 A2 | 6/2008 |

OTHER PUBLICATIONS

International Search Report for PCT/US2010/021147 dated Jul. 19, 2011.

* cited by examiner

*Primary Examiner* — Gina C Justice
(74) *Attorney, Agent, or Firm* — Fitzpatrick, Cella, Harper & Scinto

(57) ABSTRACT

Hair treatment compositions are disclosed comprising a β-amino ester compound in a cosmetically acceptable vehicle, such as a spray or cream. In embodiments, the compounds include a polybutadiene moiety. Methods of treating hair with the compositions to impart volume, texture and definition are also disclosed.

12 Claims, No Drawings

BETA-AMINO ESTER COMPOUNDS AND USES THEREOF

CROSS-REFERENCE TO RELATED APPLICATIONS

This application is a divisional of U.S. application Ser. No. 12/354,697, filed Jan. 15, 2009, the entire contents of which are incorporated herein by reference.

BACKGROUND OF THE INVENTION

1. Field of the Invention

The invention is directed to compositions and methods for treating hair, and in particular to methods and compositions for imparting thickness, volume, texture and definition, which permit improved styling.

2. Description of Related Art

Hair treatment products on the market typically use commercial polymers to impart volume, texture, definition and thickness. People with fine or thin hair regularly use "volumizing" products in the form of shampoos, conditioners, styling sprays, creams, gels, or mousses in an effort to increase the volume and body of their hair. Many of these materials are polyvinylpyrrolidone/polyvinyl acetate (PVP/VA) combinations. These materials create volume in hair by binding multiple hair fibers together in spot-welds, such that a droplet of the product lands on a section of the hair thereby linking a hair fiber back on itself and/or linking two or more fibers, creating stiffer hair, more resistant to, for example, falling flat on the head. This technology suffers from several drawbacks, as the visual benefits obtained do not last and the hair is left feeling stiff or crunchy. Thus, it is desired to identify and develop compositions that achieve these results with greater ease of use, less heaviness and less feeling of sticky residue, that do not impart a crunchy or stiff feeling to the hair, and which impart shine and softness to the hair as well as volume and thickness.

Preparation of poly(β-amino esters) from conjugate addition of bis(secondary amines) or primary amines to a bis(acrylate ester) is described in U.S. Pat. Nos. 6,998,115 and 7,427,394, and related applications, the disclosures of which are incorporated herein by reference in their entirety. Many of the compounds within the scope of the disclosure are said to be biodegradable and biocompatible and said to be useful in a variety of drug delivery systems. However, use in cosmetics is not contemplated in these patents.

SUMMARY OF THE INVENTION

Whereas advances in the art typically involve new formulations of known compounds, the inventors herein have brought real innovation to the field of hair treatment at the compound level, developing new molecular entities for use in styling hair. Of particular interest are hair styling compositions that avoid reliance on conventional high-molecular weight PVP/VA compounds, that provide a lighter, more natural feel, while still providing thickness, texture, volume and definition.

In one aspect, the invention involves the use of the compounds such as are disclosed in U.S. Pat. Nos. 7,427,394 and 6,998,115; U.S. Patent Application Publication Nos. 2004/0071654 and U.S. 2005/0265961; and International Application Nos. WO 02/31025; WO 04/106411 and WO 07/143659 with a cosmetically acceptable carrier in a composition for treatment of hair. The disclosure of each of the aforesaid patents and published applications is incorporated by reference herein.

Thus, in one aspect, the invention is a hair treatment composition comprising a compound according to formula (I) or (I') in a cosmetically acceptable carrier:

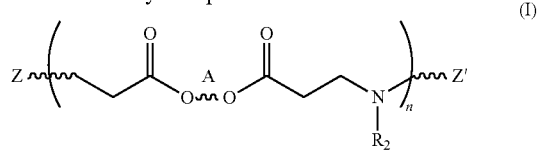

(I)

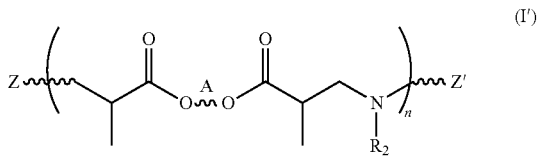

(I')

In formula (I) and (I'), n is an integer between 1 and 10,000; and Z and Z', together with the atoms to which they are attached, represent acrylate, methacrylate or amino end groups.

The substituent $R_2$ is the residue of a primary amine starting material, which may be reacted with a diacrylate or dimethacrylate starting material, to form the compound according to formula (I) or (I'), as described in greater detail below. For example, $R_2$ may be selected from the group consisting of alkyl, alkenyl, alkynyl, acyl, alkoxy, alkoxyalkyl, amino, aminoalkyl, aryl, heteroaryl, amido, alkylthioether, carbamoyl, carbonyldioxyl, carboxyl ester, cyclic aliphatic, cyclic heteroaliphatic, aromatic, heteroaromatic and ureido groups, each of which groups may be substituted with at least one substituent selected from the group consisting of alkyl, alkenyl, alkynyl, acyl, alkoxy, alkoxylalkyl, amino, aminoalkyl, aryl, heteroaryl, amido, cyclic aliphatic, heterocyclic aliphatic, halogen, hydroxyl, cyano, carbamoyl, carboxylic acid, carbonyldioxyl, alkylthioether, siloxyl, and thiohydroxyl groups.

A is a carbon chain or a heteroatom-containing carbon chain, optionally substituted with at least one substituent selected from the group consisting of alkyl, alkenyl, alkynyl, amino, alkylamino, dialkylamino, trialkylamino, aminoalkyl aryl, ureido, heterocyclic, aromatic heterocyclic, cyclic, aromatic cyclic, halogen, hydroxyl, alkoxy, cyano, amido, carbamoyl, carboxylic acid, ester, carbonyl, carbonyldioxyl, alkylthioether, and thiol groups; wherein said substituents may join to form one or more rings.

Alternatively, a bis(amine) is used as a starting material and is reacted with the diacrylate or dimethacrylate starting material so that the hair treatment composition comprises a compound according to formula (II) or (II').

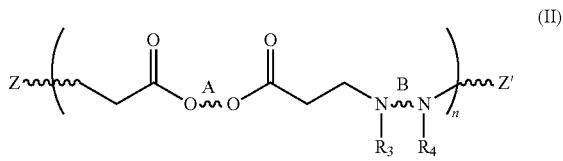

(II)

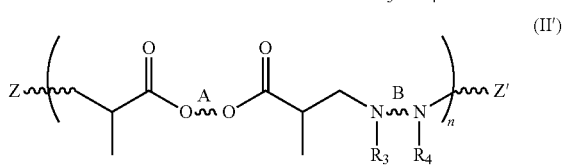

(II')

In formula (II) and (II'), A, n, Z and Z' are as defined for formula (I); $R_3$ and $R_4$ are defined as for $R_2$ in Formula (I); and B and A are, independently, a carbon chain or a heteroatom-containing carbon chain, optionally substituted with at least one substituent selected from the group consisting of alkyl, alkenyl, alkynyl, amino, alkylamino, dialkylamino, trialkylamino, aminoalkyl, aryl, ureido, heterocyclic, aromatic heterocyclic, cyclic, aromatic cyclic, halogen, hydroxyl, alkoxy, cyano, amido, carbamoyl, carboxylic acid, ester, carbonyl, carbonyldioxyl, alkylthioether, and thiol groups.

In another aspect of the invention, oligomers are provided which have β-amino ester monomer units bonded to blocks of repeating monomer units (such as polybutadiene blocks). In particular, it has now been found that compounds having a β-amino ester moiety and a rubber moiety in novel and useful hair treatment compositions avoid the drawbacks of the volumizing products known in the prior art.

Without wishing to be bound by any particular theory, it is believed that the β-amino ester compounds disclosed herein bind to the hair fibers to increase inter-fiber friction and produce benefits not delivered through conventional technology. The inventive composition increase friction in hair while allowing hair fibers to remain free to move, allowing for a more natural feel. In addition, the inventive compositions afford longer lasting and re-shapeable hair styles. Fibers are free to separate and re-attach at different points, allowing for a more natural feel and movement. These effects are achieved according to the invention using the compositions and methods described herein. As a result, the present inventive compositions and methods are believed to avoid making the hair feel stiff or crunchy.

Thus, in this further aspect, the invention is a hair treatment composition comprising a compound according to formula (I) or formula (II) wherein A is a rubber moiety, such as, without limitation, a moiety made up of one or more units of butadiene, isoprene, chloroprene, styrene-butadiene, mixtures thereof, or variations thereof.

In preferred embodiments, a hair treatment composition according to the invention comprises a compound of formula (III) in a cosmetically acceptable carrier:

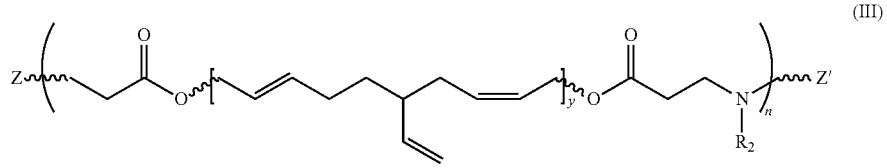

(III)

In the above formula (III), n is an integer between 1 and 10,000; y is an integer between 1 and 10,000; and $R_2$ is selected from the group consisting of alkyl, alkenyl, alkynyl, acyl, alkoxy, alkoxyalkyl, amino, aminoalkyl, aryl, heteroaryl, amido, alkylthioether, carbamoyl, carbonyldioxyl, carboxyl ester, cyclic aliphatic, cyclic heteroaliphatic, aromatic, heteroaromatic and ureido groups, each of which groups may be substituted with at least one substituent selected from the group consisting of alkyl, alkenyl, alkynyl, acyl, alkoxy, alkoxylalkyl, amino, aminoalkyl, aryl, heteroaryl, amido, cyclic aliphatic, heterocyclic aliphatic, halogen, hydroxyl, cyano, carbamoyl, carboxylic acid, carbonyldioxyl, alkylthioether, siloxyl, and thiohydroxyl groups.

Alternatively, a hair treatment composition according to the invention may comprise a compound according to formula (IV) in a cosmetically suitable carrier, wherein y, n, Z, Z', B, $R_3$ and $R_4$ are all defined as set forth above with respect to formulas (I), (II) and (III):

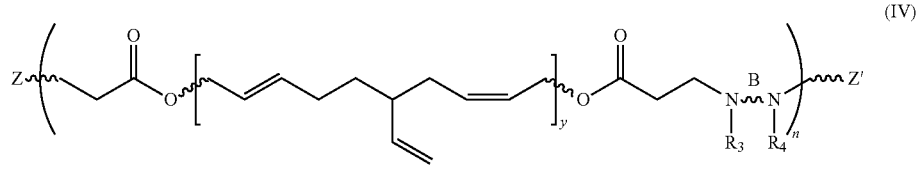

(IV)

Methods according to the invention comprise the step of contacting scalp hair with the composition containing a compound according to any of formulas (I) through (IV) in a cosmetically acceptable carrier, as described in greater detail in the detailed description that follows.

DETAILED DESCRIPTION OF THE PREFERRED EMBODIMENTS

The advantages of the compositions and formulations according to the invention are brought about by incorporating specific β-amino ester moieties and specific linking moieties according to the invention. In some cases (not to be construed as limiting), the formulations have been adapted for shaping hair. It has been found that some of these compositions afford the user the ability not only to shape the hair, but the ability to reshape a style after it has been significantly altered (after a night's sleep for example). The methods and specific examples of reacting diacrylates and amines, and the compounds and functional results achieved thereby, are described in greater detail in the following detailed description of the invention.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75th Ed., and specific functional groups are generally defined as described therein. Additionally, general principles of organic chemistry, as well as specific functional moieties and reactivity, are described in Organic Chemistry, Thomas Sorrell, University Science Books, Sausalito (1999), the entire contents of which are incorporated herein by reference.

Unless expressly stated otherwise, the compounds and groups described herein may be substituted with any number of substituents or functional moieties permitted by the valences of the respective compound or group. In general, the term "substituted" whether preceded by the term "optionally" or not, and substituents contained in formulas of this invention, refer to the replacement of hydrogen atoms in a given structure with a specified substituent. Unless stated otherwise, when more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. For purposes of this invention, heteroatoms such as nitrogen, oxygen or sulfur, may be bonded to hydrogen atoms or be substituted with any permissible substituents of organic compounds described herein which satisfy the valencies of the heteroatoms.

Where a carbon atom in a chain may be replaced with a heteroatom, this is also sometimes referred to as a "substitution."

The term acyl as used herein refers to a group having the general formula —C(O)R, where R is alkyl, alkenyl, alkynyl, aryl, carbocylic, heterocyclic, or aromatic heterocyclic. An example of an acyl group is acetyl.

As used herein, an acrylate radical, and/or end group has the structure

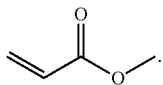

A methacrylate radical and/or end group has the structure

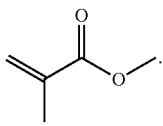

The term aliphatic, as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties.

The term alkyl as used herein refers to a saturated, straight- or branched-chain hydrocarbon radicals derived from a hydrocarbon containing between one and twenty carbon atoms by removal of a single hydrogen atom. In some embodiments, the alkyl group contains 1-10 carbon atoms. In another embodiment, the alkyl group contains 1-8 carbon atoms. In still other embodiments, the alkyl group contains 1-6 carbon atoms. In yet another embodiment, the alkyl group contains 1-4 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. As used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl," and the like, encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

The term alkoxy as used herein refers to a saturated (i.e., alkyl-O—) or unsaturated (i.e., alkenyl-O— and alkynyl-O—) group attached to the parent molecular moiety through an oxygen atom. In certain embodiments, the alkyl, alkenyl or alkynyl group contains 1-20 aliphatic carbon atoms. In certain other embodiments, the alkyl, alkenyl, and alkynyl groups employed in the alkoxy groups of the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples include, but are not limited to, methoxy, ethoxy, propoxy, isopropoxy, n-butoxy, tert-butoxy, i-butoxy, sec-butoxy, neopentoxy, n-hexoxy, and the like.

The term alkenyl denotes a monovalent group derived from a hydrocarbon moiety having at least one carbon-carbon double bond by the removal of a single hydrogen atom. In certain embodiments, the alkenyl group employed in the invention contains 1-20 carbon atoms. In some embodiments, the alkenyl group employed in the invention contains 1-10 carbon atoms. In another embodiment, the alkenyl group employed contains 1-8 carbon atoms. In still other embodiments, the alkenyl group contains 1-6 carbon atoms. In yet another embodiments, the alkenyl group contains 1-4 carbons. Alkenyl groups include, for example, ethenyl, propenyl, butenyl, 1-methyl-2-buten-1-yl, and the like.

The term alkynyl as used herein refers to a monovalent group derived from a hydrocarbon having at least one carbon-carbon triple bond by the removal of a single hydrogen atom. In certain embodiments, the alkynyl group employed in the invention contains 1-20 carbon atoms. In some embodiments, the alkynyl group employed in the invention contains 1-10 carbon atoms. In another embodiment, the alkynyl group employed contains 1-8 carbon atoms. In still other embodiments, the alkynyl group contains 1-6 carbon atoms. Representative alkynyl groups include, but are not limited to, ethynyl, 2-propynyl(propargyl), 1-propynyl, and the like.

The term alkylamino, dialkylamino, and trialkylamino as used herein refers to one, two, or three, respectively, alkyl groups, as previously defined, attached to the parent molecular moiety through a nitrogen atom. The term alkylamino refers to a group having the structure —NHR' wherein R' is an alkyl group, as previously defined; and the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. In certain embodiments, the alkyl group contain 1-20 aliphatic carbon atoms. In certain other embodiments, the alkyl group contains 1-10 aliphatic carbon atoms. In yet other embodiments, the alkyl group contains 1-8 aliphatic carbon atoms. In still other embodiments, the alkyl group contain 1-6 aliphatic carbon atoms. In yet other embodiments, the alkyl group contain 1-4 aliphatic carbon atoms. Additionally, R', R", and/or R'" taken together may optionally be —(CH$_2$)$_k$— where k is an integer from 2 to 6, to form a ring. Examples include, but are not limited to, methylamino, dimethylamino, ethylamino, diethylamino, diethylaminocarbonyl, methylethylamino, iso-propylamino, piperidino, trimethylamino, and propylamino.

An amino group, as used herein, encompasses alkylamino, dialkylamino and trialkylamino groups (as defined above), and aminoalkyl likewise includes —RNH$_2$, —RNHR', —RNR'R" and —RNR'R"R'". In preferred embodiments according to the invention, a substituted aminoalkyl group, such as a diethanolaminopropyl group, is substituted on the nitrogen of the β-amino ester moiety of the compound.

The term aromatic, as used herein, refers to a moiety having delocalized electrons due to conjugated double bonds, which may form a ring (as in an aryl moiety); heteroaromatic means an aromatic compound in which a carbon is replaced with one or more nitrogen, oxygen, phosphorus, silicon or sulfur atoms.

In general, the terms aryl and heteroaryl, as used herein, refer to mono- or polycyclic, heterocyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments of the present invention, aryl refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term heteroaryl, as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term carboxylic acid as used herein refers to a group of formula —CO$_2$H.

The terms halo and halogen as used herein refer to an atom selected from fluorine, chlorine, bromine, and iodine.

The term heteroaliphatic, as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term heterocyclic, as used herein, refers to an aromatic or non-aromatic, partially unsaturated or fully saturated, 3- to 10-membered ring system, which includes single rings of 3 to 8 atoms in size and bi- and tri-cyclic ring systems which may include aromatic five- or six-membered aryl or aromatic heterocyclic groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring.

The term aromatic heterocyclic, as used herein, refers to a cyclic aromatic radical having from five to ten ring atoms of which one ring atom is selected from sulfur, oxygen, and nitrogen; zero, one, or two ring atoms are additional heteroatoms independently selected from sulfur, oxygen, and nitrogen; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. Aromatic heterocyclic groups can be unsubstituted or substituted with substituents selected from the group consisting of branched and unbranched alkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide.

The term carbonyldioxyl, as used herein, refers to a carbonate group of the formula —O—CO—OR.

The term carbamoyl, as used herein, refers to an amide group of the formula —CONH$_2$.

The term hydrocarbon, as used herein, refers to any chemical group comprising hydrogen and carbon. The hydrocarbon may be substituted or unsubstituted. The hydrocarbon may be unsaturated, saturated, branched, unbranched, cyclic, polycyclic, or heterocyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, and the like. As would be known to one skilled in this art, all valencies must be satisfied in making any substitutions.

The term thiohydroxyl or thiol, as used herein, refers to a group of the formula —SH.

The term ureido, as used herein, refers to a group of the formula —NH—CO—NH$_2$

The following are more general terms used throughout the present application:

As used herein, the singular forms "a", "an", and "the" include the plural reference unless the context clearly indicates otherwise. Thus, for example, a reference to "a monomer" includes a plurality of such monomers.

The term "keratin" as used herein refers any one of a class of fibrous structural proteins found in hair, wool, and nails. Keratin proteins contains a large quantity of cysteine residues. Human hair is a keratin that has approximately 15% cysteine residues cross-linked by disulfide bridges.

As used herein, a "monomer" is a repeating structural unit appearing in a polymer or an oligomer. Thus, for example, the polymer polybutadiene is comprised of repeating units derived from butadiene.

The term "oligomer," as used herein, refers to a chemical compound with less than 10 repeating structural units. In particular, a compound according to the invention containing less than 10 β-amino ester groups is considered an oligomer, notwithstanding the size of the block connecting the amino ester groups.

The term "polymer," as used herein, refers to a chemical compound of repeating structural units (monomers) connected by covalent bonds. A polymer is typically of high molecular weight comprising 10 s to 100 s to 1000 s or even more monomers. However, as used herein, the term "polymer" also includes "oligomers."

The term "rubber," as used herein, means a compound containing repeating units of butadiene, isoprene, chloroprene, styrene-butadiene, or variations thereof, and also includes ethylene vinyl acetate (EVA) (such as sold under the tradename Elvax®), urethane rubber, silicone rubber or silicone elastomer. These units incorporated in a molecule constitute the "rubber moiety" of the molecule, as that term is used herein.

The symbol ~~~ in a chemical structure means that different atoms and/or bonds may be found at that position. Thus, in formula (I), A is designated with symbol ~~~ because a number of options exist for the configuration of A. In connection with the end groups, to form an acrylate or methacrylate end group, for example, Z ~~~ means that Z and the carbon to which it is attached form a CH$_2$= terminus of the acrylate or methacrylate end group. Alternatively, in the same formula, the ~~~ symbol may represent a bond with the next monomer repeat group.

Preferred Embodiments

Hair treatment compositions according to the invention comprise a β-amino ester compound which may be formed by reacting a diacrylate or dimethacrylate with an amine according to one of the following general reaction schemes:

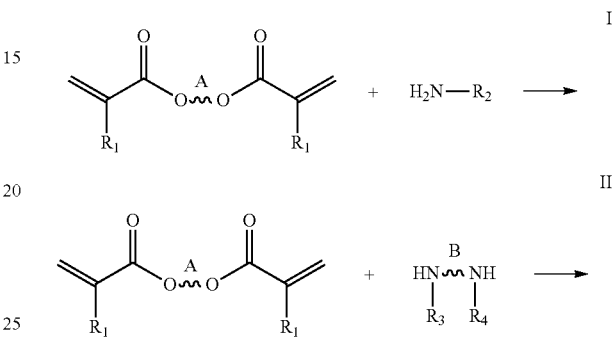

In these formulas R$_1$ is a hydrogen or methyl, which defines the starting material as a diacrylate or a dimethacrylate. R$_2$, R$_3$, and R$_4$ are selected from the group consisting of alkyl, alkenyl, alkynyl, acyl, alkoxy, alkoxyalkyl, amino, aminoalkyl, aryl, heteroaryl, amido, alkylthioether, carbamoyl, carbonyldioxyl, carboxyl ester, cyclic aliphatic, cyclic heteroaliphatic, aromatic, heteroaromatic and ureido groups, each of which groups may be substituted with at least one substituent selected from the group consisting of alkyl, alkenyl, alkynyl, acyl, alkoxy, alkoxylalkyl, amino, aminoalkyl, aryl, heteroaryl, amido, cyclic aliphatic, heterocyclic aliphatic, halogen, hydroxyl, cyano, carbamoyl, carboxylic acid, carbonyldioxyl, alkylthioether, siloxyl, and thiohydroxyl groups.

If the starting material is a dimethacrylate, the above reactions form compounds represented by the corresponding formulas (I') and (II"), wherein A, B, Z, Z' and n are as defined above for formulas (I) and (II):

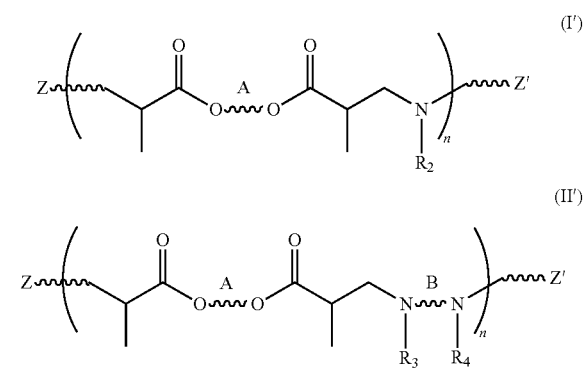

Where the starting material is a diacrylate, the above reactions form compounds represented by the corresponding formulas (I) and (II):

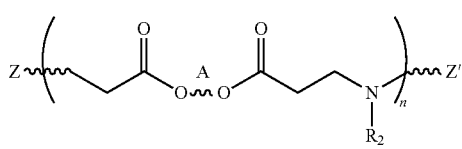 (I)

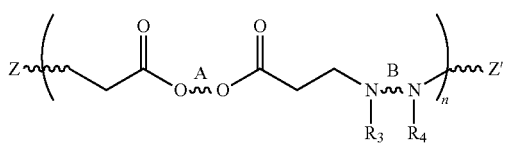 (II)

Such compounds include, without limitation, the compounds disclosed in the aforementioned patents and published applications incorporated by reference.

In an embodiment of the present invention, n is in the range of 1 to 10,000. In certain other embodiments of the present invention, n is in the range of 1 to 1,000, 1 to 100 or 3 to 10.

In preferred embodiments, the acrylate or methacrylate moieties in the compounds are linked by a relatively high molecular weight moiety A. In the presently preferred embodiments, A is a rubber moiety, including without limitation, a material comprising monomers selected from butadiene, styrene-butadiene, chloroprene, and isoprene monomers.

Rubber-containing materials that may be reacted to form a polymer according to the invention include, without limitation, polybutadiene diacrylate, which is represented by the formula

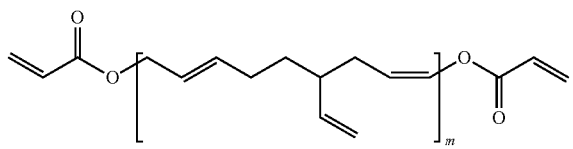

or its corresponding dimethacrylate.

Polyisoprene diacrylate may also be used, represented by the following formula,

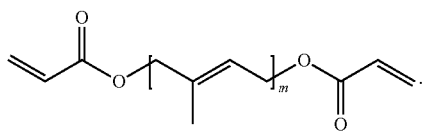

The corresponding dimethacrylate may also be used.

In these starting materials m may be 1 to 60, and in certain embodiments 1 to 40, 1 to 30 or 20 to 30.

Alternatively, polychloroprene or styrene-butadiene rubbers may be modified into diacrylates or dimethacrylates, which can then be reacted according to the general reaction schemes I and II above. Styrene/butadiene rubbers have the following general structure:

$[(CH_2-CH=CH-CH_2)_{\overline{m}}CH-CH_2]_n$.

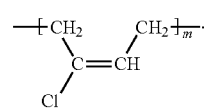

Poly-chloroprene has the general structure

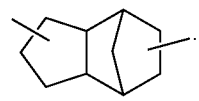

In presently preferred embodiments polybutadiene diacrylates (PBDs) are employed as a starting material. Although not limiting the invention, diacrylates and dimethacrylates having a number average molecular weight in the range of 1000 g/mol to 5,000 g/mol may be used. In the examples elaborated below, two different starting material were used, having a number average molecular weight of 1400 g/mol and 3000 g/mol, respectively.

In other embodiments, A is an optionally substituted carbon chain or heteroatom containing carbon chain containing 1 to 30 atoms in the chain. Thus, in some instances, 1,4-butanediol diacrylate, 1,4-butanediol dimethacrylate, 1,2-ethanediol diacrylate, 1,6-hexanediol diacrylate, 2,5-hexanediol diacrylate, and 1,3-propanediol diacrylate may be used as a diacrylate starting material, such that A comprises a carbon chain having less than 30 atoms.

The linker A between the acrylate or methacrylate moieties of the compound may comprise a substituted carbon chain wherein the substituents join to form one or more rings. For example, such multicyclic moiety A may be represented by the formula The corresponding compound useful in a hair treatment composition according to the invention has the following formula, wherein Z, Z' and $R_2$ are as described above.

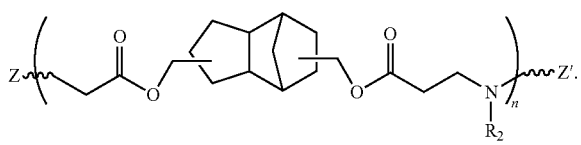

Alternatively, linker A may comprise a carbon chain or heteroatom-containing carbon chain having one or more aromatic substituents on the chain, resulting in compounds according to the following formula,

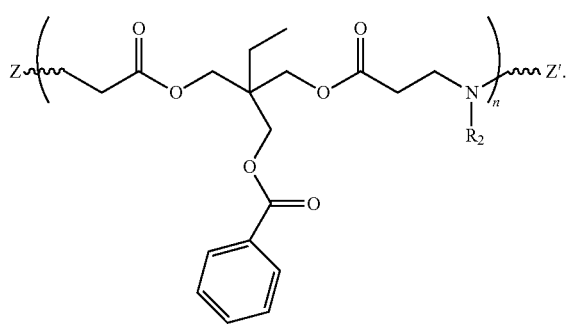

The diacrylate or dimethacrylate starting material may be reacted with amines having varying functional groups at varying ratios. For example, acceptable PBD:amine ratios may range from about 1:2 to about 2:1. In the examples elaborated below, PBD:amine ratios were varied between 1:1.8 and 1:1.2.

The compounds according to the invention, resulting from the above-described reaction, sometimes have small amounts of unreacted amine. In preferred embodiments, the compound used in the composition according to the invention contains less than 1 wt %, preferably less than 0.1 wt %, and more preferably less than 0.01 wt % unreacted amine.

A suitable diacrylate or dimethacrylate may be reacted with a primary amine having a formula $NH_2R_2$ (where $R_2$ is as defined above) by Michael Addition. The $R_2$ group on the primary amine may be selected to impart desired properties to the composition. Thus, the amine may be selected to modify the properties imparted to the composition by the rubber moiety, to reduce a greasy, heavy feel while maintaining the frictional attributes obtained with the rubber, for example. Alternatively, hydrophilic groups may be incorporated into the compound via the amine to improve water solubility. Likewise, hydrophobic groups may be used to improve oil phase formulation and/or interaction with hair lipids. Aromatic moieties and styrene-containing moieties may be used to increase the stiffness of the finished compounds.

The following primary amines have been used to formulate compounds according to the invention: propylamine; butylamine; pentylamine; hexylamine; octylamine; 1-aminodecane; isopropylamine; sec-butylamine; isobutylamine; tert-butylamine; 2-aminopentane; isopentylamine; 2-amino-6-methylheptane; 3-(dimethylamino)-1-propylamine; 2-diethylaminoethylamine; 2-(diisopropylamino)ethylamine; 3-(diethylamino)propylamine; N,N-dimethylethylenediamine; ethanolamine; 3-amino-1-propanol; amino-2-propanol; 4-amino-1-butanol; 5-amino-1-pentanol; 6-amino-1-hexanol; n-(3-aminopropyl)diethanolamine; 2-(2-aminoethoxy)ethanol; 2-methoxyethylamine; 3-methoxypropylamine; 3-ethoxypropylamine; 3-butoxypropylamine; aminoacetaldehyde dimethyl acetal; 3-Isopropoxypropylamine; aminoacetaldehyde diethyl acetal; 4-aminobutyraldehyde diethyl acetal; 3-aminopropyltriethoxysilane; 2-methoxybenzylamine; 4-methoxybenzylamine; 2-phenoxyethylamine; 3,4-dimethoxyphenethylamine; 4-methoxyphenethylamine; 2-methoxyphenethylamine; tyramine; benzylamine; 4-methylbenzylamine; phenethylamine; 4-aminobenzylamine; 4-tert-butylbenzylamine; 4-phenylbenzylamine; 4-iodobenzylamine; 4-(aminomethyl)pyridine; 3-picolylamine; 2-fluorobenzylamine; 4-fluorobenzylamine; 4-fluorophenethylamine; 3-(trifluoromethyl)benzylamine; 2,2,3,3,4,4,5,5,6,6,7,7,8,8,9,9-heptadecafluorononylamine; cyclopropylamine; cyclopentylamine; N-(3-aminopropyl)-2-pyrrolidinone; cyclohexylamine; cyclohexanemethylamine; 2-(1-cyclohexenyl)ethylamine; 1-(2-aminoethyl)piperidine; 3-morpholinopropylamine; (±)-3-amino-1,2-propanediol; 2-amino-1,3-propanediol; 2-Amino-2-methyl-1,3-propanediol; 2-amino-2-ethyl-1,3-propanediol; N,N-bis(2-hydroxyethyl)ethylenediamine; oxamic Acid; and 2-amino-2-(hydroxymethyl)propane-1,3-diol.

Suitable amines containing siloxyl substituents may be used as starting materials, including, without limitation, 3-aminopropyl(diethoxy)methylsilane; 3-(2-aminoethylamino) propyldimethoxymethylsilane; N-[3-(trimethoxysilyl)propyl]ethylenediamine; 3-[2-(2-aminoethylamino)ethylamino]propyl-trimethoxysilane; and 1-[3-(trimethoxysilyl)propyl]urea.

The amino acids, including Alanine, Leucine, Serine, Cysteine, Tyrosine, Glutamic Acid, Glutamine, Lysine, and Arginine are also suitable to form compounds according to the invention.

Alternatively, a bis(amine) starting material may be used. The amine groups in such bis(amine) starting materials are linked by a moiety B, as shown in reaction scheme II above. In general B is a carbon chain or a heteroatom-containing carbon chain, optionally substituted with at least one substituent selected from the group consisting of alkyl, alkenyl, alkynyl, amino, alkylamino, dialkylamino, trialkylamino, aminoalkyl aryl, ureido, heterocyclic, aromatic heterocyclic, cyclic, aromatic cyclic, halogen, hydroxyl, alkoxy, cyano, amido, carbamoyl, carboxylic acid, ester, carbonyl, carbonyldioxyl, alkylthioether, and thiol groups.

Bis(secondary amine) monomers that are useful in the present invention include, but are not limited to, N,N'-dimethylethylenediamine, piperazine, 2-methylpiperazine, 1,2-bis(N-ethylamino)ethylene, and 4,4'-trimethylenedipiperidine.

End groups Z and Z', together with the atoms to which they are attached, represent acrylate, methacrylate or amino end group. In embodiments, Z and Z' form an amino group or unsaturated acrylate or methacrylate group on both termini of the polymer. Thus, for example, in the case where Z and Z' form an amino moiety, Z' is hydrogen and Z is —$NR_2$—H. Where the end group is acrylate, Z ∿∿∿ means that Z and the carbon to which it is attached form a $CH_2$= terminus of the acrylate or methacrylate end group while Z' forms an acrylate or methacrylate group.

Non-limiting examples of polymers with amine terminated end groups and acrylate terminated end groups are:

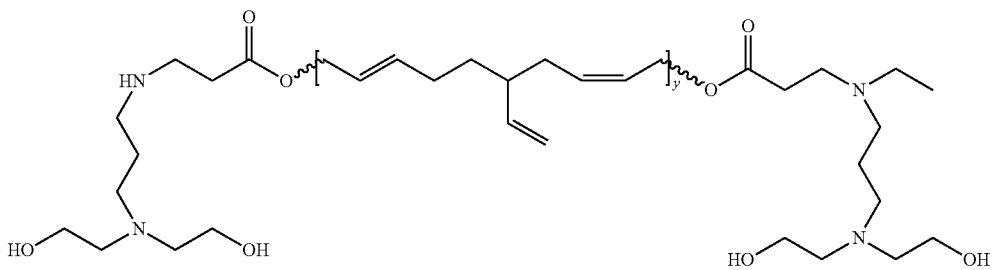

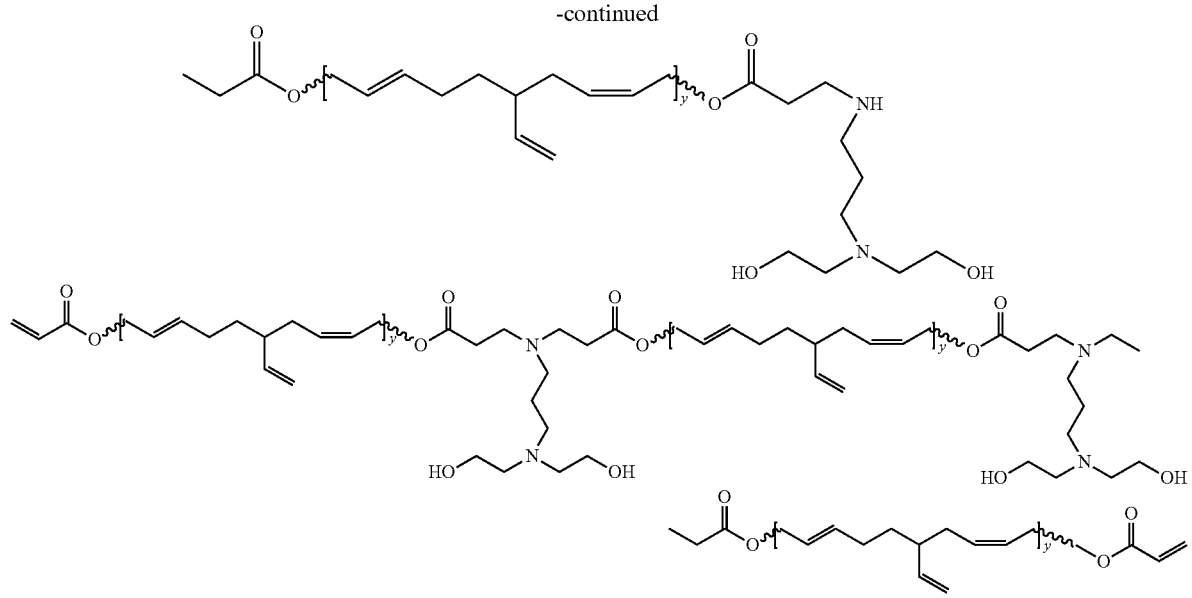

wherein y is 1 to 100.

In embodiments, n in formulas (I) to (IV) may range from 1 to 10,000. However, presently preferred compounds of the invention are oligomers, having 3 to 10 amino ester units. A composition according to the invention may contain a plurality of oligomers of different length.

The preferred compositions used in the invention include a cosmetically acceptable carrier such that the composition can be applied to the hair without irritation to the eyes or scalp. The compositions may be in the form of an oil-in-water emulsion, a water-in-oil emulsion, a dispersion, a suspension, a cream, a foam, a gel, a spray, a powder, a liquid or a pomade.

The β-amino ester compound is generally present in the composition in a range of about 0.01 percent by weight to about 20 percent by weight of the composition. In embodiments, the β-amino ester is present in a range of about 0.1 percent by weight to about 10.0 percent by weight of the composition; and in still other embodiments in a range of about 1.0 percent by weight to about 5.0 percent by weight.

The compositions according to the invention are preferably water or water-alcohol based, meaning that that they contain greater than 50 percent by weight water. Preferably water is present in the compositions according to the invention in a range of 60 to 99 percent by weight of the composition. In the presently preferred embodiments, water is present in a range of about 80 to about 95 percent by weight of the composition.

The cosmetically acceptable carrier for the compound contains ingredients conventionally used in hair treatment compositions. One or more emulsifiers may be included in a range of about 0.1 to about 10.0 percent by weight, in preferred embodiments, in a range of about 0.5 percent by weight to about 3.0 percent by weight. Suitable formulation amounts may be determined by those of ordinary skill in the art without undue experimentation, depending on how the composition is intended to be delivered. Suitable emulsifiers may be selected from those known in the art, including without limitation, Polysorbate 20, Polyacrylate-13, Polyisobutene, Oleth-10, and the like.

A fatty alcohol, or a mixture, may be provided in an amount of 0.1 to about 5.0 percent by weight of the composition to provide thickening and/or emollient properties. In embodiments, a fatty alcohol component such as cetearyl alcohol (a mixture of fatty alcohols), may be provided in a range of about 0.1 to 1.0 percent by weight of the composition.

One or more fatty acids may be provided in a range of about 0.1 percent by weight to 5.0 percent by weight of the composition. Fatty acids, include without limitation, palmitic acid, stearic acid, linoleic acid, myristic acid, and others known in the art to provide thickening and/or emollient properties in a hair treatment composition.

Compositions according to the invention may also include at least one additive conventionally used in hair treatment compositions. Non-limiting examples of suitable additives include emollients, processing aids, dyes, anionic surfactants, cationic surfactants, nonionic surfactants, amphoteric surfactants, fragrances, screening agents, preserving agents, proteins, vitamins, silicones, polymers such as thickening polymers, plant oils, mineral oils, synthetic oils and any other additive conventionally used in compositions for the care and/or treatment of keratinous fibers.

General Synthetic Procedure

The synthesis of the compounds described below was performed in 30 ml clear glass jars with phenolic caps lined with polyethylene core liners, and stirred with 15.9×9.5 mm Teflon® coated spin bar. For each reaction, 5 g of PBD was added to each vial Amine was added by pipette for liquids or by mass for solids at desired ratios. Vials were stirred at 90° C. for 48 hours. The spin bar was removed while the reaction material was still hot. Polymers were allowed to cool to room temperature before observing for color and viscosity as a rough monitor of reaction completeness. As the reactions went to completion, the viscosity dramatically increased and the mixtures turned more yellow/amber in color. Products were stored at 4° C.

Primary amines were obtained from Sigma-Aldrich, Inc. (St. Louis, Mo.) and VWR International, LCC (West Chester, Pa.). PBDs were obtained from Sartomer Company, Inc. (Exton, Pa.) (Sartomer product #CN307) and San Esters (New York, N.Y.) (product #BAC-15 and BAC-45).

Example 1-1

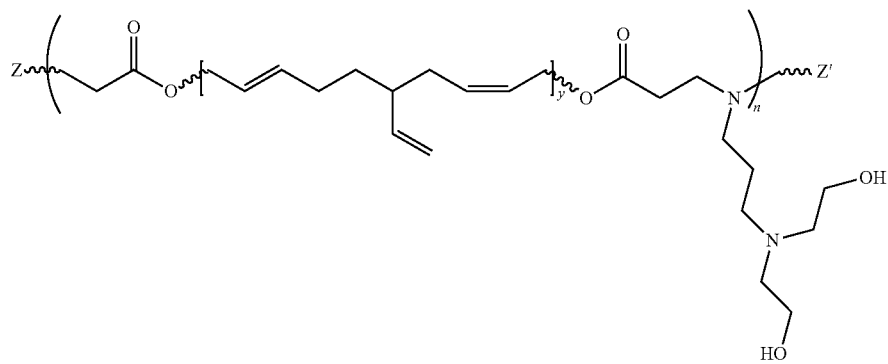

The above polymer was synthesized following the procedure outlined above using 5.0 grams of polybutadiene diacrylate (99%) having a molecular weight of 3000 Da (1 equivalent) and 325.11 mg of N-(3-aminopropyl) diethanolamine (1.2 equivalents). The resulting material was characterized via $^1$H NMR.

HNMR (CDCl$_3$): δ (ppm) 1.0-1.3 (m), 1.3-1.5 (m), 1.6-1.7 (m), 1.8-2.2 (m), 2.4-2.5 (m), 2.5-2.7 (m), 2.7-2.8 (m), 3.6-3.7 (m), 4.8-5.1 (m), 5.2-5.4 (m), 5.4-5.7 (m).

All NMR spectra were recorded on a Varian Mercury 300 MHz spectrometer and taken in CDCl3.

In like manner, Examples 1-2 through 1-11 below were formed from polybutadiene diacrylate polymer (molecular weight 1400 Da or 3000 Da) and suitable amines to form the β-amino ester compounds listed below. Compositions were formulated and tested as set forth below.

Example 1-2

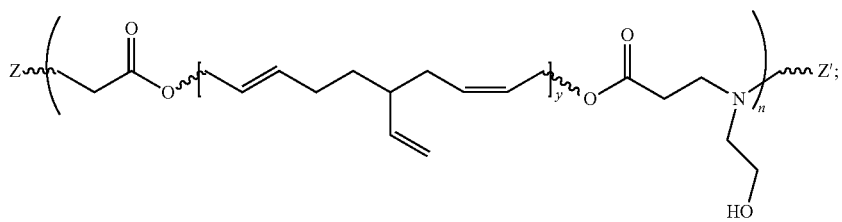

Example 1-3

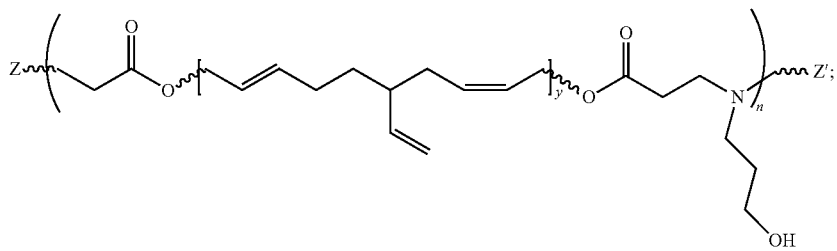

Example 1-4

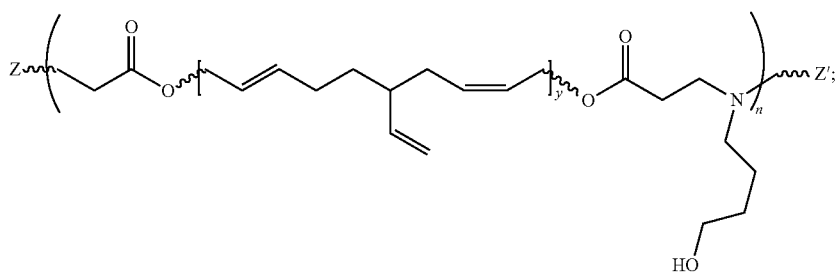

Example 1-5
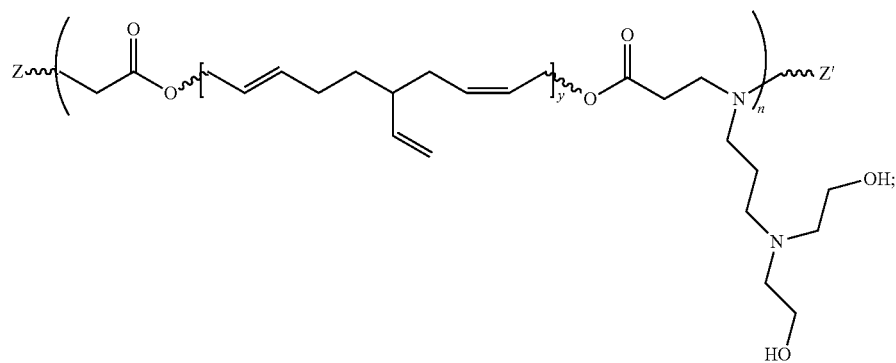
Example 1-6
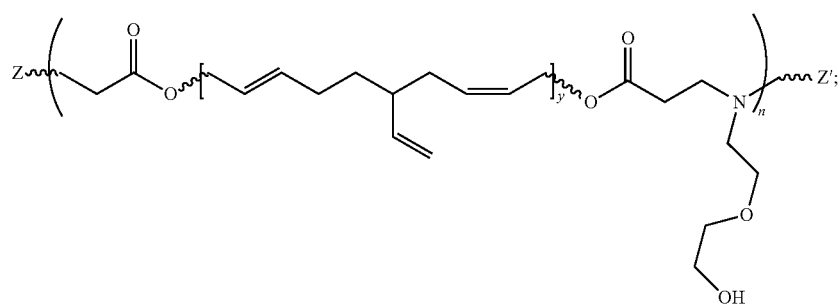
Example 1-7
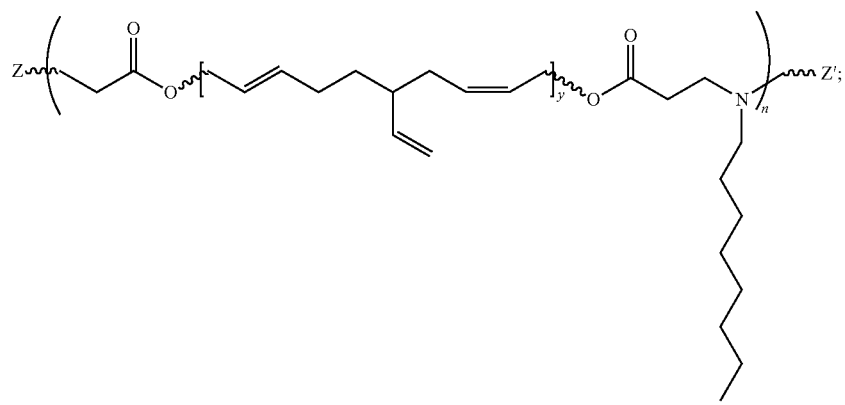

Example 1-8
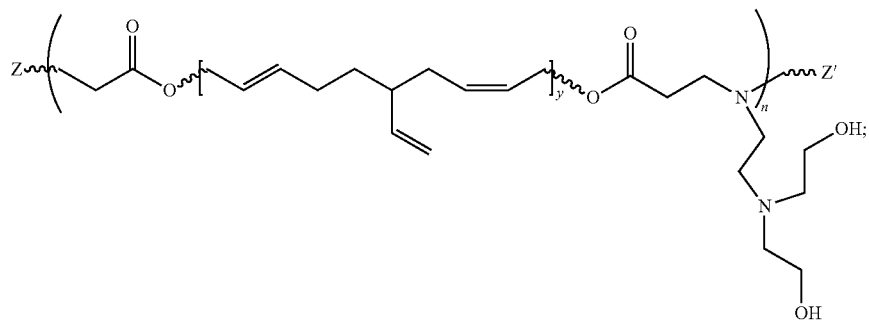
Example 1-9
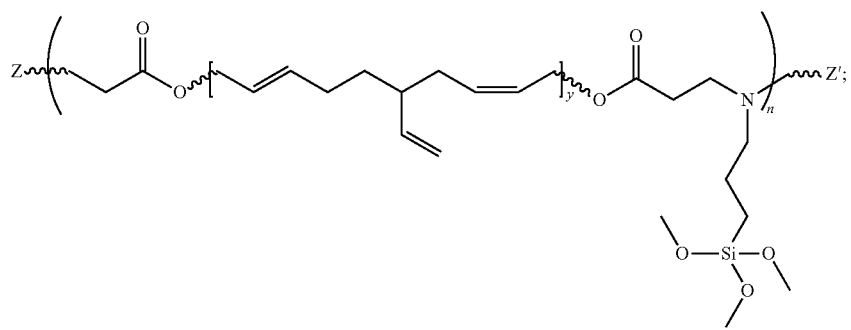
Example 1-10
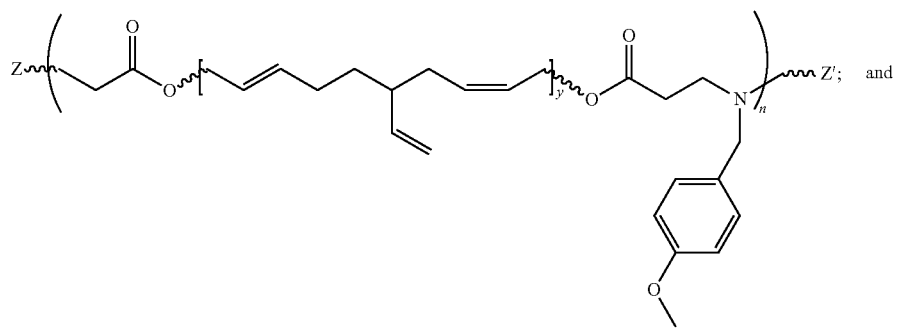
Example 1-11
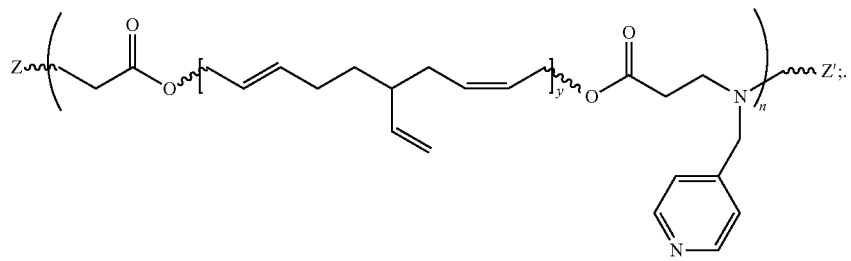

Example 2-1

Feel Test

The feel properties of preferred polymers on hair were assessed. 10 g of a 1% (w/w) in THF solution was prepared. Solutions were applied to dry 1 g×2.5 cm wide×22 cm long hair tresses of virgin straight medium brown hair (International Hair Importers). Tresses were curled with a ½ in. diameter curling iron (Hot Tools Model 1101) on the highest heat setting (approximately 200° C.) for 30 seconds. Each tress was evaluated with clean hands for the following attributes: tack, grease, friction, and the presence of a coating. Each attribute was rated against the following scale: 0=none, 1=slight, 2=moderate, 3=excessive.

The desired feel properties are no grease, no tackiness, very little coating or none at all, and slight friction. The results obtained in Table 1 were exemplary of preferred compositions, based on the feel properties obtained.

TABLE 1

| Compound | Tack | Grease | Coating | Friction |
|---|---|---|---|---|
| PBD:amine 1:1.2 | | | | |
| 14PBD:octylamine | 0 | 0 | 1 | 0 |
| 14PBD:amino 2-propanol | 0 | 0 | 1 | 0 |
| 14PBD:n-(3-aminopropyl) diethanolamine | 0 | 0 | 0 | 2 |
| 14PBD:4-methoxybenzylamine | 0 | 0 | 1 | 0 |
| 14PBD:4-(Aminomethyl)pyridine | 0 | 0 | 1 | 0 |
| 30PBD:3-amino-1-propanol | 0 | 0 | 1 | 0 |
| 30PBD:4-amino-1-butanol | 1 | 0 | 0 | 0 |
| 30PBD:2-(2-Aminoethoxy)ethanol | 1 | 0 | 0 | 0 |
| PBD:amine 1:1.8 | | | | |
| 14PBD:3-aminopropyltriethoxysilane | 0 | 0 | 2 | 0 |
| 14PBD:4-Methoxybenzylamine | 1 | 0 | 1 | 0 |
| 14PBD:4-(Aminomethyl)pyridine | 0 | 0 | 1 | 0 |
| 30PBD:ethanolamine | 1 | 0 | 0 | 0 |
| 30PBD:n-(3-aminopropyl) diethanolamine | 0 | 0 | 0 | 1 |

14PBD means polybutadiene diacrylate having a molecular weight of 1400 Da.
30PBD means polybutadiene diacrylate having a molecular weight of 3000 Da.

Example 3-1

Snap and Movement Test

The movement of hair treated with each polymer in Table 1 was assessed. A 1% (w/w) solution of 10 g of each polymer in THF was prepared. Solutions were applied to dry 1 g×2.5 cm wide×22 cm long hair tresses of virgin straight medium brown hair (International Hair Importers). Tresses were curled with a ½ inch diameter curling iron (Hot Tools Model 1101) on the highest heat setting (approximately 200° C.) for 30 seconds. Once cool, the ends of the tress were extended to full length and released. Snap is defined as the initial recoil of the tress, while movement is defined as the length of time after the initial recoil that the tress was in motion, as well as the intensity of motion. Both attributes were rated against the following scale: 0=poor, 1=ok, 2=good, 3=great, 4=excellent. Scores of 4 for both snap and movement were desired.

The results for snap and movement for thirteen compounds tested are given in Table 2.

TABLE 2

| Compound | Snap | Movement |
|---|---|---|
| PBD:amine (1:1.2) | | |
| 14PBD:octylamine | 3 | 3 |
| 14PBD:amino 2-propanol | 2 | 2 |
| 14PBD:n-(3-aminopropyl) diethanolamine | 3 | 3 |
| 14PBD:4-methoxybenzylamine | 3 | 3 |
| 14PBD:4-methoxybenzylamine | 3 | 3 |
| 30PBD:4-(Aminomethyl)pyridine | 2 | 2 |
| 30PBD:3-amino-1-propanol | 0 | 0 |
| 30PBD:4-amino-1-butanol | 2 | 2 |
| PBD:amine 1:1.8 | | |
| 14PBD:3-aminopropyltriethoxysilane | 3 | 3 |
| 14PBD:4-Methoxybenzylamine | 3 | 3 |
| 14PBD:4-(Aminomethyl)pyridine | 3 | 3 |
| 30PBD:Ethanolamine | 3 | 3 |
| 30PBD:n-(3-aminopropyl) diethanolamine | 2 | 2 |

The polymers on Table 3 were chosen as exhibiting better properties based on the overall results obtained in the feel and the snap/movement tests. Feel scores were given more weight than snap/movement scores as feel is a more desirable property.

TABLE 3

| Compound | Tack | Grease | Coating | Friction | Snap | Movement |
|---|---|---|---|---|---|---|
| PBD: amine1: 1.2 | | | | | | |
| 14PBD: octylamine | 0 | 0 | 1 | 0 | 3 | 3 |
| 14PBD: amino 2-propanol | 0 | 0 | 1 | 0 | 2 | 2 |
| 14PBD: n-(3-aminopropyl) diethanolamine | 0 | 0 | 0 | 2 | 3 | 3 |
| 14PBD: 4-methoxybenzylamine | 0 | 0 | 1 | 0 | 3 | 3 |
| 14PBD: 4-methoxybenzylamine | 0 | 0 | 1 | 0 | 3 | 3 |

Example 4-1

Consumer Use Test

β-amino ester compound according to Example 1-1 was formulated into a cream according to Formulation Example 5-1 below and a cream according to Formulation Example 5-2. These two formulations were given to 20 women. The women in the study were blinded to the ingredients and the potential performance benefits of the formulations. The women were asked to use each product for one week. Typically, the formulations were applied to wet hair and blown dry to a desired style. After using the two formulations, the women were interviewed and asked to fill out a product performance survey. The needs of the 20 women compared to how the two formulations delivered against those needs are shown in Table 4.

TABLE 4

| Desired Benefit | Priority | Benefit Delivered From Cream | Benefit Delivered From Spray |
|---|---|---|---|
| Volume and body | High | High | Med |
| Thickening | High | High | Med |

TABLE 4-continued

| Desired Benefit | Priority | Benefit Delivered From Cream | Benefit Delivered From Spray |
|---|---|---|---|
| Weightlessness | High | High | Med |
| Lasting Effect | High | High | Low |
| Ease of Achieving Effect | High | Med | Low |
| Lack of Residue | Med | Med | Low |
| Softness | Low | Med | Low |
| Shine/Conditioning | Med | Med | Low |
| Smoothness | Med | Med | Low |
| Hold/Control/Texture | Med | Med | Low |
| Ease of Use | Med | Med | High |
| Pleasant Smell | Med | Low | Low |

Formulation Example 5-1

A styling cream containing β-amino ester compound according to the invention may include the following:

| Ingredients | % w/w |
|---|---|
| Water | q.s. |
| β-amino ester compound | 0.50-6.00 |
| Polysorbate 20 (and) Polyacrylate-13 (and) Polyisobutene (Emulsifier) | 0.50-4.00 |
| Fragrance | 0.20-3.00 |
| Phenoxyethanol (and) Methylisothiazolinone (Preservative) | 0.50-1.50 |
| PPG-2 Myristyl Ether Propionate (Emollient) | 0.10-5.00 |
| Oleth-10 (Emulsifier) | 0.10-2.00 |

Formulation Example 5-2

A styling cream containing β-amino ester compound was prepared with the following ingredients:

| Ingredients | % w/w |
|---|---|
| Water | 93.00 |
| β-amino ester compound | 3.00 |
| Polysorbate 20 (and) Polyacrylate-13 (and) Polyisobutene | 1.45 |
| Fragrance | 1.00 |
| Phenoxyethanol (and) Methylisothiazolinone | 0.50 |
| PPG-2 Myristyl Ether Propionate | 0.50 |
| Oleth-10 | 0.50 |

The above composition was manufactured using the process described below.

A vessel was charged with water (Phase A) and heated to 75° C. Phase B consisting of polysorbate 20, polyacrylate-13, and polyisobutene was added to Phase A using high agitation and allowed to mix for 30 minutes or until homogeneous. The β-amino ester compound, oleth-10, and PPG-2 myristyl ether propionate were mixed in a separate vessel at 75° C. until homogeneous to form Phase C. Phase C was added to the above mixture of Phase A and Phase B and the contents were mixed until homogeneous. The mixture was cooled to 40° C. Thereafter, Phase D, consisting of phenoxyethanol, and methylisothiazolinone, was added to the above mixture and the contents were mixed until homogeneous. The mixture was cooled to 30° C. Phase E, consisting of fragrance, was added to the above mixture and the contents were mixed until homogeneous. Water (q.s.) was added to the mixture and homogenized to obtain the above composition.

Formulation Example 5-3

A styling spray containing β-amino ester compound according to the invention may include the following:

| Ingredients | % w/w |
|---|---|
| Water | q.s. |
| β-amino ester compound | 0.50-6.00 |
| Oleth-10 (Emulsifier) | 0.10-10.00 |
| Ethoxydiglycol Oleate (Emollient) | 0.10-5.00 |
| Fragrance | 0.20-3.00 |
| Phenoxyethanol (and) Methylisothiazolinone (Preservative) | 0.50-1.50 |
| Sodium Chloride | 0.10-1.50 |
| Xanthan Gum (Rheology modifier) | 0.10-1.50 |

Formulation Example 5-4

A styling spray containing β-amino ester compound was prepared with the following ingredients:

| Ingredients | % w/w |
|---|---|
| Water | 92.70 |
| β-amino ester compound | 3.00 |
| Oleth-10 | 1.10 |
| Ethoxydiglycol Oleate | 1.00 |
| Fragrance | 1.00 |
| Phenoxyethanol (and) Methylisothiazolinone | 0.50 |
| Sodium Chloride | 0.40 |
| Xanthan Gum | 0.30 |

The above composition may be manufactured using the process described below.

A vessel was charged with water and xanthan gum was added to form Phase A. Xanthan gum was allowed to hydrate for 20 minutes. Phase A was then heated to 75° C. In a separate vessel, the β-amino ester compound, oleth-10 and ethoxydiglycol oleate were heated to 75° C. and mixed to form a homogeneous Phase B. Phase B was added to Phase A and mixed until homogeneous. The mixture was cooled to 40° C. Thereafter, Phase C, consisting of phenoxyethanol and methylisothiazolinone, was added to the above mixture and the contents mixed until homogeneous. The mixture was cooled to 30° C. Then, Phase D consisting of sodium chloride and fragrance was added to the above mixture and the contents were mixed until homogeneous. Water (q.s.) was added to the mixture and homogenized to obtain the above composition.

Formulation Example 5-5

A styling non-aerosol mousse containing β-amino ester compound according to the invention may include the following:

| Ingredients | % w/w |
|---|---|
| Water | q.s. |
| β-amino ester compound | 0.50-6.00 |
| Cocamidopropylamine Oxide (Surfactant) | 0.10-10.00 |

-continued

| Ingredients | % w/w |
|---|---|
| Oleth-10 (Emulsifier) | 0.10-10.00 |
| Ethoxydiglycol Oleate (Emollient) | 0.10-5.00 |
| Fragrance | 0.20-3.00 |
| Phenoxyethanol (and) Methylisothiazolinone (Preservative) | 0.50-1.50 |
| Sodium Chloride | 0.10-1.50 |
| Xanthan Gum (Rheology modifier) | 0.10-1.50 |

Formulation Example 5-6

A styling non-aerosol mousse containing β-amino ester compound was prepared with the following ingredients:

| Ingredients | % w/w |
|---|---|
| Water | 89.70 |
| β-amino ester compound | 3.00 |
| Cocamidopropylamine Oxide | 3.00 |
| Oleth-10 | 1.10 |
| Ethoxydiglycol Oleate | 1.00 |
| Fragrance | 1.00 |
| Phenoxyethanol (and) Methylisothiazolinone | 0.50 |
| Sodium Chloride | 0.40 |
| Xanthan Gum | 0.30 |

The above composition was manufactured using the process described below.

To form Phase A, a vessel was charged with water and xanthan gum. Xanthan gum was allowed to hydrate for 20 minutes. Phase A was then heated to 75° C. To obtain Phase B, β-amino ester compound, oleth-10 and ethoxydiglycol oleate were heated to 75° C. in a separate vessel. The contents were mixed until homogeneous. Phase B was added to Phase A and mixed until homogeneous. The mixture was cooled to 40° C. Thereafter, Phase C, consisting of phenoxyethanol and methylisothiazolinone, was added to the above mixture and the contents were mixed until homogeneous. The mixture was cooled to 30° C. Thereafter, Phase D, consisting of Cocamidopropylamine oxide, sodium chloride and fragrance was added to the above mixture of Phases A, B, and C until a homogeneous composition above was obtained. Water (q.s.) was added to the mixture and mixed until homogeneous.

Notwithstanding anything herein to the contrary, the foregoing embodiments are exemplary only and not to be considered as limiting the invention, which is defined by the appended claims.

What is claimed is:

1. A compound according to formula (I):

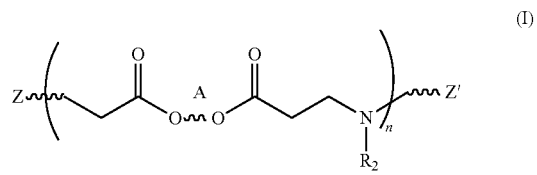

wherein n is an integer between 1 and 10,000;
Z and Z', together with the atoms to which they are attached, represent acrylate, methacrylate or amino end groups;
$R_2$ is selected from the group consisting of alkyl, alkenyl, alkynyl, acyl, alkoxy, alkoxyalkyl, amino, aminoalkyl, aryl, heteroaryl, amido, alkylthioether, carbamoyl, carbonyldioxyl, carboxyl ester, cyclic aliphatic, cyclic heteroaliphatic, aromatic, heteroaromatic and ureido groups, each of which groups may be substituted with at least one substituent selected from the group consisting of alkyl, alkenyl, alkynyl, acyl, alkoxy, alkoxylalkyl, amino, aminoalkyl, aryl, heteroaryl, amido, cyclic aliphatic, heterocyclic aliphatic, halogen, hydroxyl, cyano, carbamoyl, carboxylic acid, carbonyldioxyl, alkylthioether, siloxyl, and thiohydroxyl groups; and
A is a rubber moiety with a molecular weight in a range of about 1000 g/mol to about 10,000 g/mol selected from the group consisting of butadiene, chloroprene, isoprene, and styrene-butadiene units.

2. The compound according to claim 1, wherein A consists of butadiene units.

3. The compound according to claim 2, wherein $R_2$ is selected from the group consisting of alkyl, acyl, amino, aminoalkyl, alkoxy, alkoxyalkyl, amido, each of which groups may be substituted with at least one substituent selected from the group consisting of alkoxy, alkoxylalkyl, amino, aminoalkyl, heteroaryl, amido, halogen, hydroxyl, cyano, carbamoyl, carboxylic acid, carbonyldioxyl, alkylthioether, siloxyl, and thiohydroxyl groups.

4. The compound according to claim 3, wherein $R_2$ is alkyl or aminoalkyl group substituted with at least one substituent selected from the group consisting of alkoxy, alkoxylalkyl, amino, aminoalkyl, heteroaryl, amido, halogen, hydroxyl, cyano, carbamoyl, carboxylic acid, carbonyldioxyl, alkylthioether, siloxyl, and thiohydroxyl groups.

5. The compound according to claim 3, wherein $R_2$ is hydroxyl substituted aminoalkyl.

6. The compound according to claim 2, wherein n is 1 to 100.

7. The compound according to claim 1, wherein the compound has the structure selected from the group consisting of:

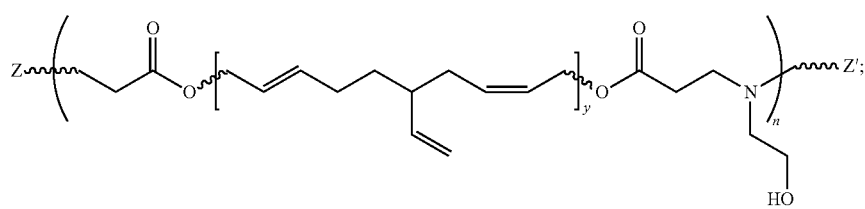

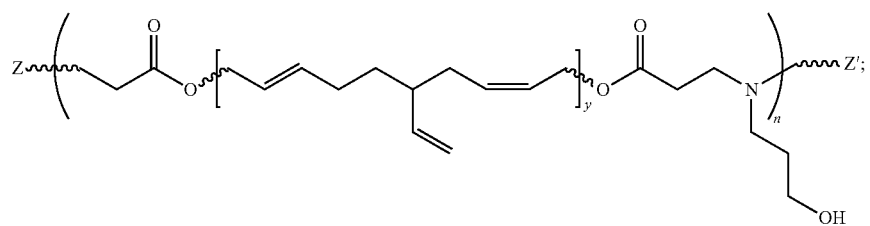
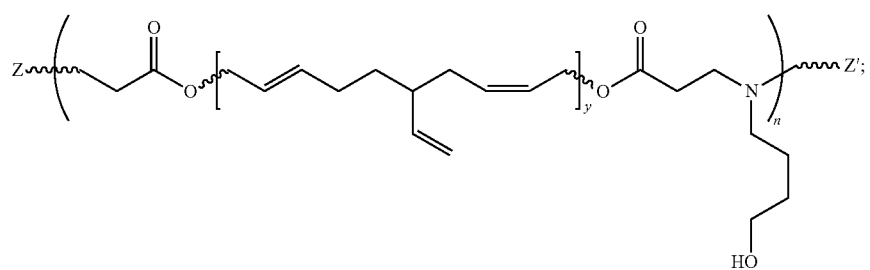
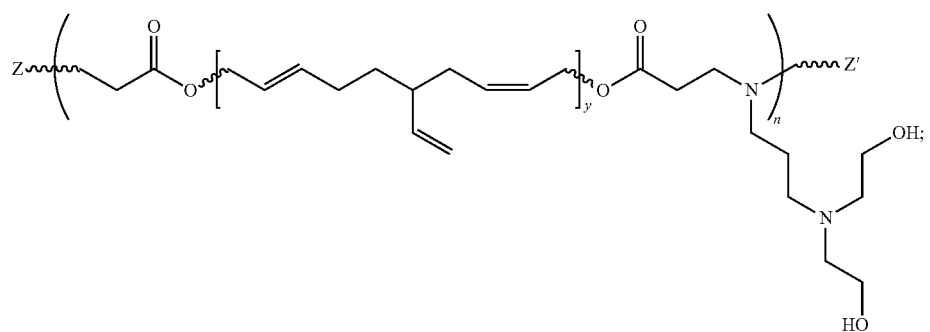
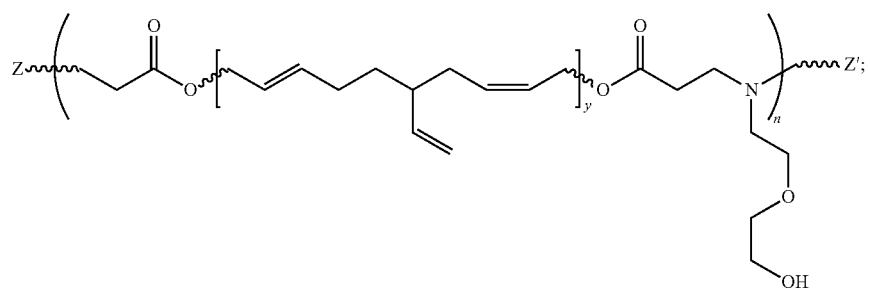
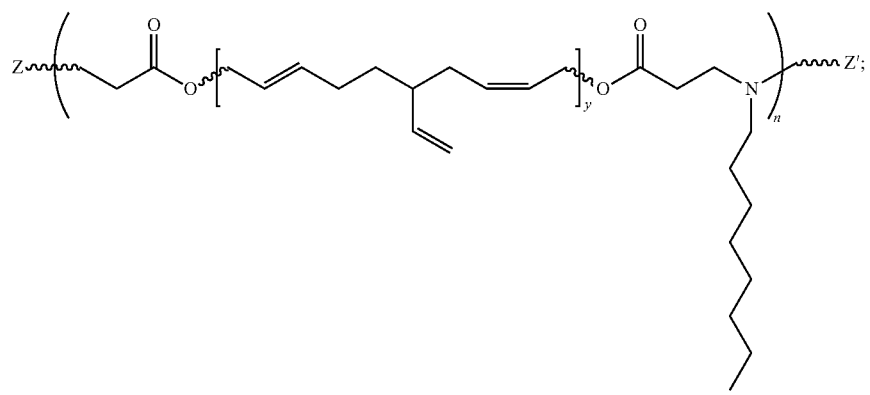

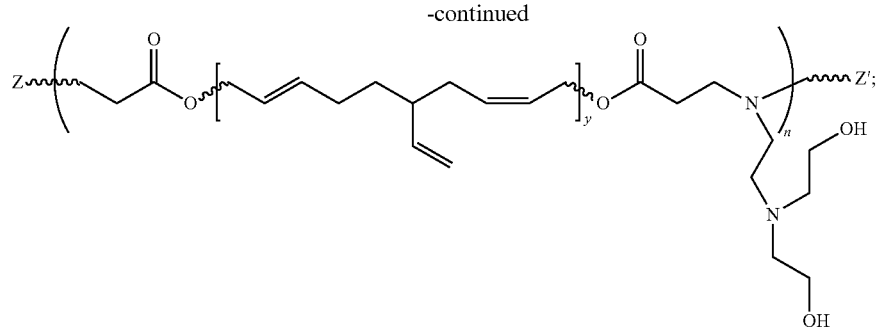
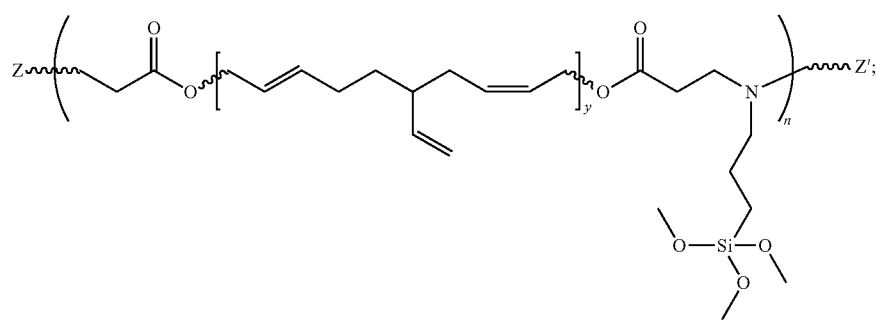
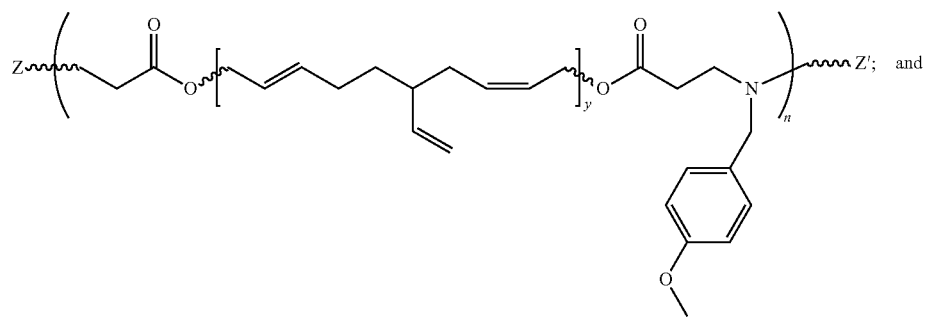
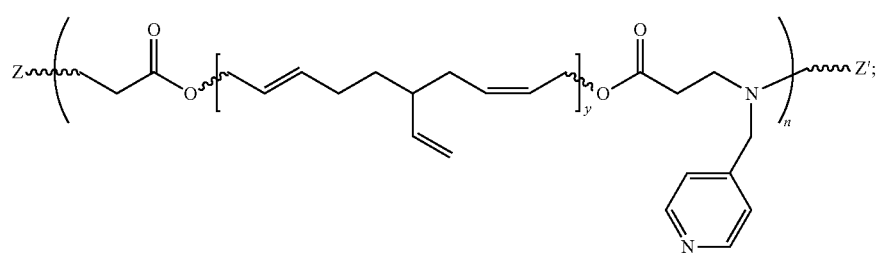
wherein y is an integer from 1 to 100;
n is 1 to 100; and
Z and Z', together with the atoms to which they are attached, form an acrylate, methacrylate, or amino end group.

8. A compound having the structure:

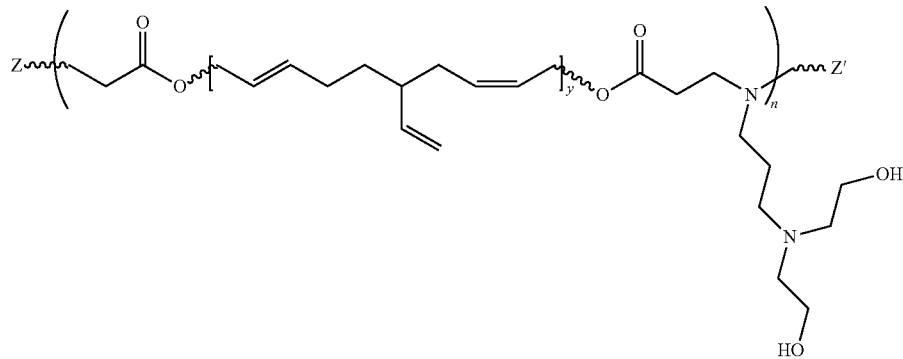

wherein y is an integer from 1 to 100;

n is 1 to 100; and

Z and Z', together with the atoms to which they are attached, form an acrylate, methacrylate, or amino end group.

9. A hair treatment composition comprising a compound according to claim 1 and a cosmetically acceptable carrier.

10. The hair treatment composition of claim 9, wherein the composition is a hair styling product, shampoo, or conditioner.

11. The hair treatment composition of claim 10 wherein the hair styling product is a spray, cream, gel, mousse, or pomade.

12. A method of treating scalp hair comprising applying to the hair the composition according to claim 9.

* * * * *